United States Patent
Hood

[11] Patent Number: 5,510,928
[45] Date of Patent: Apr. 23, 1996

[54] MULTIPLE PASS OPTICAL FILTER

[75] Inventor: Patrick J. Hood, Thousand Oaks, Calif.

[73] Assignee: Rockwell International Corporation, Seal Beach, Calif.

[21] Appl. No.: 433,626

[22] Filed: Nov. 7, 1989

[51] Int. Cl.$^6$ .................. G02F 1/03; G02B 5/22
[52] U.S. Cl. ........................... 359/241; 359/887
[58] Field of Search ................. 350/164, 166, 350/169, 171, 172, 173, 286, 600, 618, 622, 311, 354, 363; 372/11, 98; 359/887, 241

[56] References Cited

U.S. PATENT DOCUMENTS

| | | | |
|---|---|---|---|
| 2,881,663 | 4/1959 | Dearborn | 350/622 |
| 3,289,099 | 11/1966 | Masters | 372/11 |
| 3,365,678 | 1/1968 | Maurer | 372/11 |
| 3,415,602 | 12/1968 | Harrick | 350/286 |
| 3,531,183 | 9/1970 | Aagard | 350/622 |
| 3,575,490 | 4/1971 | Reisman . | |
| 3,623,797 | 11/1971 | Daw . | |
| 3,904,981 | 9/1975 | Hughes et al. | 372/98 |
| 4,156,209 | 5/1979 | Herbst et al. | 372/98 |
| 4,420,217 | 12/1983 | Gerharz . | |

FOREIGN PATENT DOCUMENTS

| | | | |
|---|---|---|---|
| 0214045 | 3/1987 | European Pat. Off. | 350/311 |
| 3633126 | 3/1988 | Germany | 350/397 |
| 0029842 | 3/1980 | Japan | 350/311 |
| 1099303 | 6/1984 | U.S.S.R. | 350/166 |
| 1265678 | 10/1986 | U.S.S.R. | 350/166 |

Primary Examiner—Stephen C. Buczinski
Attorney, Agent, or Firm—John C. McFarren

[57] ABSTRACT

A method and apparatus are provided for filtering incident radiation to protect imaging sensors from the damaging effects of high intensity radiation. The apparatus comprises a filter and a plurality of mirrors disposed within a cube. The filter is positioned diagonally within the cube so that portions of the incident radiation reflected by the filter are directed to a beam-stop on a surface of the cube. Portions of the radiation passed by the filter are directed by the mirrors to pass through the filter a plurality of times. Passing the radiation through a single filter a plurality of times provides a high density imaging system in a physically compact geometric shape. A focused beam passes through the filter in regions of successively greater optical gain. High intensity radiation thermally activates the filter to reject the radiation and protect the sensors. Activation of the filter proceeds in stakes starting with the region of the filter receiving the highest optical gain so that the filter is also protected from damaging radiation.

12 Claims, 1 Drawing Sheet

MULTIPLE PASS OPTICAL FILTER

TECHNICAL FIELD

The present invention relates to optical filtering devices and, in particular, to a compact optical device having a filter and a plurality of mirrors placed within a cube for passing an image through the filter multiple times without distortion.

BACKGROUND OF THE INVENTION

Imaging systems with high optical gain are inherently susceptible to sensor damage from high intensity radiation, whether the sensor is the human eye or a solid state device. As modern solid state detectors have become more sensitive, the susceptibility to damage from high intensity radiation has also increased. In both military and civilian environments, high intensity radiation, such as used in laser range finders, is becoming more common. Thus, there is a need for systems and methods to protect optical sensors from damage resulting from accidental or deliberate exposure to high intensity radiation.

In the prior art there are two general methods for protecting sensors from high energy radiation. A first method is to block selectively those wavelengths at which high energy radiation is encountered. This can be achieved, for example, by using dyed plastic filters in the visible spectrum or interference filters in the infrared spectrum. Dyed plastics have a limitation, however, in that they substantially reduce the out-of-band transmissions. That is, to achieve the necessary optical densities required for sensor protection, dyed filters also tend to restrict those wavelengths at which the received high intensity radiation does not exist. This limitation of out-of-band transmissions results in a significant reduction in detector sensitivity. Interference filters, on the other hand, provide substantially higher out-of-band transmission because of their narrow band filtering characteristics, but they generally have inadequate optical density when only one filter is used. Furthermore, specialized interference filters tend to be a relatively expensive components in an optical system.

A second method for protecting sensors is to use non-linear devices that are activated by high intensity radiation. Non-linear devices have advantages in that they can provide very high average transmittance when not subject to high energy radiation, and they can function over a wide range of high energy wavelengths, thus acting as broadband switches. However, activation of such devices often requires energy on the order of that sufficient to damage a sensor, which necessitates an intermediate focal plane. Furthermore, the protective range of non-linear devices can be limited by their own susceptibility to damage from high intensity radiation.

A situation to be avoided in systems designed to protect sensors from high intensity radiation is the reflection of incident radiation back toward the radiation source. In military environments where laser range finders are being used, for example, the reflection of incident radiation can have the adverse effect of revealing the presence and location of an optical system. Thus, a need exists for an optical imaging system that is transparent to normal radiation, that is opaque to high intensity radiation that would damage the sensors, and that reflects incident high intensity radiation harmlessly away from the direction of the radiation source.

SUMMARY OF THE INVENTION

The present invention is part of an optical imaging system that is hardened to protect the sensing elements from high intensity radiation. The invention comprises a multiple pass filter device that includes a combination of refractive and reflective elements that are configured to transmit an incident image through a single filter element more than once. The filter element may be an interference filter or a non-linear filter, for example, and the combination of optical elements is chosen to optimize the performance of the particular filter and hardening technique employed.

In the preferred embodiment of the present invention, incident radiation is collected by a lens and directed into an imaging cube. The radiation enters one face of the cube and strikes a filter at a 54.74 degree angle of incidence. The filter is positioned diagonally within the cubic lattice. A portion of the radiation is reflected into a beam-stop (which may simply comprise a black matte surface, for example, to absorb the radiation) on one surface of the cube and the balance of the radiation passes through the filter to a mirror positioned on the opposite face of the cube at a 22.5 degree angle. The radiation beam is reflected to a second mirror positioned on an adjacent face of the cube and directed through the filter a second time. A second portion of the radiation is reflected by the filter into a beam-stop and the balance of the radiation passes through to strike a third mirror. The beam is reflected to a fourth mirror and directed through the filter a third time. Again, a portion of the radiation is reflected into a beam-stop, and the remaining radiation is directed out of the imaging cube.

With the three-pass imaging cube connected to a light detector, for example, a single interference filter that reflects 90% of the incident blue light would filter out 99.9% of the blue light after three passes. Thus, the multiple pass optical filter of the present invention achieves a high optical density in a physically compact device that utilizes only one filter and that does not reflect incident radiation out of the system.

BRIEF DESCRIPTION OF THE DRAWINGS

For a more complete understanding of the present invention and for further advantages thereof, the following Description of the Preferred Embodiment makes reference to the accompanying Drawings, in which.

DESCRIPTION OF THE PREFERRED EMBODIMENT

Figure 1:
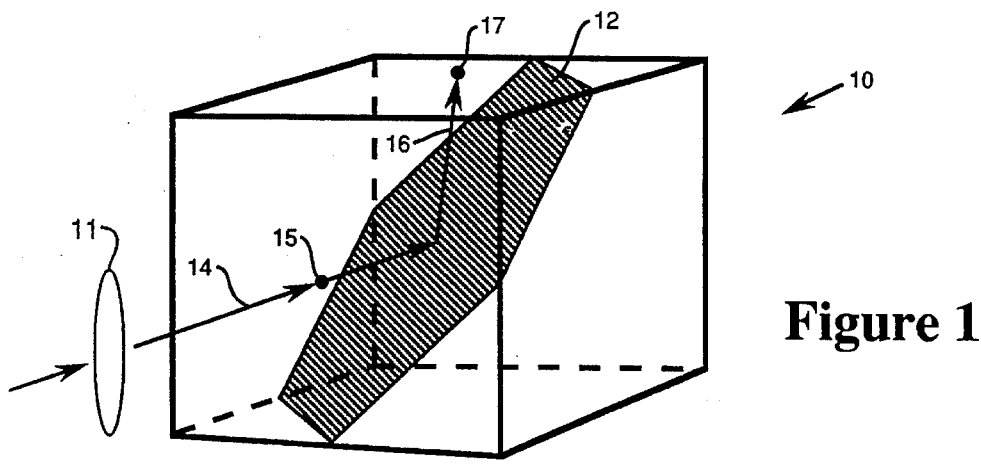
FIG. 1 is a perspective of a multiple pass optical filter of the present invention illustrating reflection of incident radiation into an energy absorbing beam-stop on the top surface of the cube.

A multiple pass filter cube 10 of the present invention is illustrated in perspective in FIG. 1. Cube 10 is the preferred embodiment of the present invention, although it will be apparent to those skilled in the art that other geometric configurations may be utilized without departing from the spirit of the present invention.

A filter 12 is disposed diagonally within cube 10 as shown in FIG. 1. Filter 12 may comprise an interference filter or a non-linear filter as is well known to those skilled in the art. In FIG. 1 filter 12 is shown with cross-hatching to highlight its orientation within cube 10 and to indicate an opaque state with respect to incident radiation. A beam 14 of incident radiation is directed through a front face of cube 12 at a point 15. Typically, beam 14 is collimated or focused by a lens 11 before being directed into cube 10. If filter 12 passes infrared radiation and beam 14 is blue light, for example, beam 14 will be reflected by filter 12 as beam 16 directed toward a point 17. A beam-stop (not shown), which may simply comprise a black matte surface, for example, may be placed at point 17 to prevent any of reflected beam 16 from being emitted by cube 10.

Figure 2:
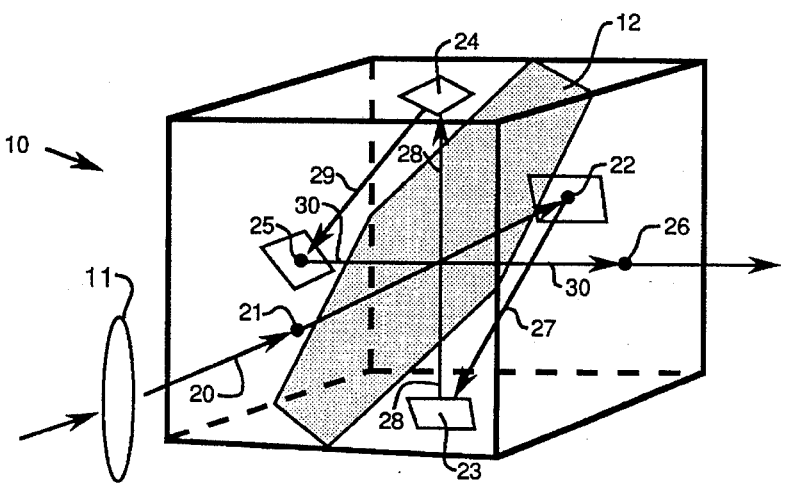
FIG. 2 is a schematic perspective of the multiple pass optical filter illustrating the path of a focused beam of incident radiation through the cube.

Referring to FIG. 2, multiple pass filter cube 10 is illustrated schematically with a beam 20 of focused radiation passing through cube 10 and filter 12. Cube 10 includes a plurality of mirrors 22, 23, 24, and 25 to direct beam 20 through cube 10. Beam 20 enters a front face of cube 20 at point 21 and passes through filter 12 to strike a mirror 22 at the back of cube 10. Mirror 22 is positioned at an angle of 22.5 degrees so as to reflect a beam 27 to a mirror 23 at the bottom of cube 10. Mirror 23 is positioned to reflect a beam 28 up through filter 12 to strike a mirror 24 at the top of cube 10. Mirror 24 is positioned to reflect a beam 29 to a mirror 25 at the left side of cube 10. Mirror 25 reflects a beam 30 through filter 12 and out a right face of cube 10 at point 26. Thus, incident beam 20 passes through filter 12 three times before becoming output beam 30. Alternatively, beam 28 could exit cube 10 at the point of mirror 24 so that incident beam 20 passes through filter 12 only twice. Configurations of the present invention other than cube 10 can be designed to direct incident beam 20 through filter 12 more than three times.

Figure 3A:
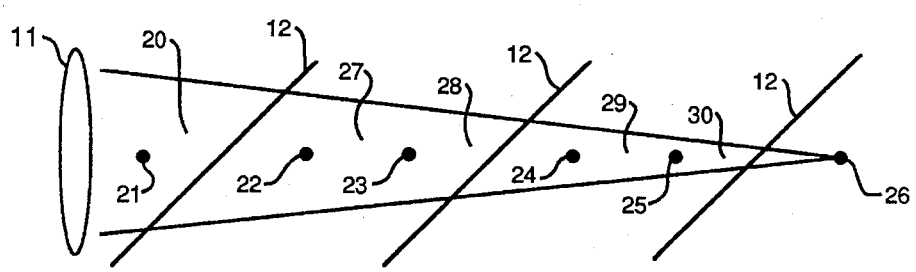
FIG. 3A is a linear schematic representation of the incident radiation focused through the filter of the multiple pass filter device three times.
Figure 3B:
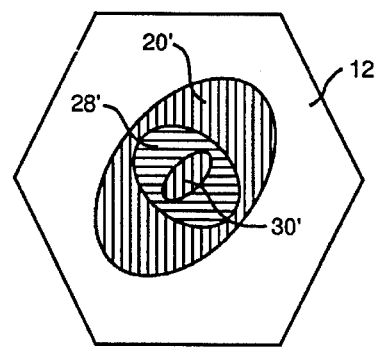
FIG. 3B is a plan view of the filter of the filter device illustrating projections of the focused beam of radiation incident on the filter for the three passes through the filter.

Referring to FIG. 3A, incident beam 20 is shown schematically in linear cross-section as a focused beam gassing through filter 12 three times and focused on point 26. Points 22, 23, 24, and 25 of FIG. 3A correspond to the mirror reflection points illustrated in FIG. 2. Thus, beam 20 becomes reflected beam 27 between points 22 and 23, reflected beam 28 between points 23 and 24, reflected beam 29 between points 24 and 25, and reflected beam 30 after point 25. Referring to FIG. 3B, projections on filter 12 of incident beam 20, reflected beam 28, and reflected beam 30 are shown as regions 20', 28', and 30', respectively, for the three passes of the focused beam through filter 12.

Providing multiple masses of a beam focused is important for improving the performance of non-linear devices such as filter 12. Referring to FIG. 3B, region 30' of filter 12 is exposed to the highest concentration of radiation and, therefore, will be the first region of filter 12 to be thermally activated by high intensity radiation. When activated, region 30' becomes opaque and/or reflective to prevent high energy radiation damage to a sensor located at or near point 26 of FIG. 3A. However, thermally activated non-linear devices also may receive thermal damage if exposed to excessive radiation for too long a period of time. Therefore, filter 12 is designed so that region 28' becomes opaque and/or reflective to block further exposure of region 30' to radiation sufficient to damage region 30'. Likewise, region 20' becomes opaque and/or reflective to block exposure of region 28' to radiation sufficient to damage region 28'. Thus, filter 12 acts as a stepped switch to protect a sensor and itself from excessive radiation. The performance of filter 12 with multiple passes of a focused beam is much greater than that of the same filter placed in a conventional single pass optical path.

Although the present invention has been described with respect to a specific embodiment thereof, various changes and modifications may be suggested to one skilled in the art. Therefore, it is intended that the present invention encompass such changes and modifications as fall within the scope of the appended claims.

I claim:

1. An optical filtering apparatus, comprising:

a filter disposed within the apparatus for receiving focused radiation entering the apparatus, said focused radiation projecting on an area of said filter;

a plurality of mirrors disposed within the apparatus;

said mirrors positioned to project said focused radiation through said filter a plurality of times in succession; and each successive projection of said focused radiation falling on a successively smaller area of said filter wholly within said area through which said focused radiation previously passed.

2. The optical filtering apparatus of claim 1, wherein said filter is disposed within the apparatus such that said focused radiation is projected on said filter at an angle other than normal to said filter.

3. The optical filtering apparatus of claim 2, wherein the apparatus comprises a cube and said filter is disposed within said cube at an angle of 54.74 degrees with respect to said focused radiation entering a first face of said cube.

4. The optical filtering apparatus of claim 3, wherein said mirrors project said focused radiation through said filter three times before said radiation exits from a second face of said cube.

5. The optical filtering apparatus of claim 4, wherein a portion of said focused radiation is reflected by said filter and absorbed within said cube.

6. A multiple pass optical filter cube, comprising:

a filter disposed diagonally within the cube for receiving focused radiation entering the cube, said focused radiation projecting on an area of said filter;

a plurality of mirrors disposed within the cube;

said mirrors positioned to project said focused radiation through said filter a plurality of times in succession; and each successive projection of said focused radiation falling on a successively smaller area of said filter wholly within said area through which said focused radiation previously passed.

7. The filter cube of claim 6, wherein said filter comprises a thermally activatable filter that becomes non-transmissive in an area where said focused radiation exceeds a predetermined intensity.

8. The filter cube of claim 7, wherein:

said focused radiation enters a front face of the cube;

said filter is disposed within the cube at an angle such that said focused radiation projects on said filter at an angle of incidence of 54.74 degrees;

a first mirror positioned at a rear face of the cube reflects a portion of said beam passing through said filter to a second mirror positioned at a bottom face of the cube;

said second mirror reflects said passed portion of said beam through said filter a second time to a third mirror positioned at a top face of the cube;

said third mirror reflects the twice passed portion of said beam to a fourth mirror positioned on a left face of the cube; and said fourth mirror reflects the twice passed portion of said beam through said filter a third time so that the third passed portion of said beam exits the cube at a right face of the cube.

9. An optical filtering device, comprising:

an activatable filter disposed diagonally within the device for receiving focused radiation incident on the device, said focused radiation projecting on an area of said filter;

a plurality of mirrors disposed within the device;

said mirrors positioned to project said focused radiation through said filter a plurality of times in succession;

each successive projection of said focused radiation falling on a successively smaller area of said filter wholly within said area through which said focused radiation previously passed; and said filter activatable to become non-transmissive to said focused radiation in an area where said focused radiation exceeds a predetermined intensity.

10. The optical filtering device of claim 9, wherein said filter is disposed within the device at an angle such that said focused radiation projects on said filter at an angle of incidence of 54.74 degrees.

11. The optical filtering device of claim 9, wherein said successively smaller areas of said filter are activatable in succession to become non-transmissive to said focused radiation when said radiation projected on each successively smaller area exceeds said predetermined intensity, the device thereby forming a stepped optical switch.

12. The optical filtering device of claim 11, wherein the device comprises a cube and said filter comprises a thermally activatable filter disposed diagonally within said cube.

* * * * *